United States Patent [19]
Crnic et al.

[11] Patent Number: 5,618,968
[45] Date of Patent: Apr. 8, 1997

[54] N-SUBSTITUTED DERIVATIVES OF N-METHYL-3-(P-TRIFLUOROMETHYL-PHENOXY)-3-PHENYLPROPYLAMINE AND THE PROCEDURE FOR THEIR PREPARATION

[75] Inventors: Zdravko Crnic, Gajnice; Srecko I. Kirin, Zagrebacka, both of Croatia

[73] Assignee: PLIVA Farmaceutska kemijska, Prehrambena i kozmeticka industrija, dionicko drustvo, Zagreb, Croatia

[21] Appl. No.: 145,141

[22] Filed: Nov. 3, 1993

[30] Foreign Application Priority Data

Feb. 5, 1993 [HR] Croatia ................. P930129A
Feb. 5, 1993 [HR] Croatia ................. P930130A

[51] Int. Cl.$^6$ ............ C07C 269/06; C07C 271/36
[52] U.S. Cl. ............... 560/27; 560/19; 560/24; 564/347; 564/348; 564/351
[58] Field of Search ............ 560/19.27; 564/347, 564/348, 351

[56] References Cited

FOREIGN PATENT DOCUMENTS

| | | |
|---|---|---|
| 0391070A1 | 3/1989 | European Pat. Off. . |
| 0380924A1 | 8/1990 | European Pat. Off. . |
| 0529842A2 | 3/1993 | European Pat. Off. . |
| 89-1015 | 3/1989 | Finland . |

OTHER PUBLICATIONS

Robertson, et al., "Synthesis of 14C– and 3H–Labaled Fluoxetine, A Selective Serotonin Uptake Inhibitor", Journal of Labelled Compounds and Radiopharmaceuticals, vol. XXIV, No. 11, (1987) pp. 1397–1404.

Cooley, et al., Amine Dealkylations with Acyl Chlorides, Synthesis No. 1, (1989) pp. 1–7.
Abstract of 89–1015, 03 Mar. 1989, Kairisalo et al., CA 114: 42266.

*Primary Examiner*—Porfirio Nazario-Gonzalez
*Assistant Examiner*—Dwayne C. Jones
*Attorney, Agent, or Firm*—Pollock, Vande Sande & Priddy

[57] ABSTRACT

The invention provides the preparation procedure for N-substituted derivatives of N-methyl-3-(p-trifluoromethylphenoxy)-3-phenylpropylamine having the general formula (I), where R is hydrogen and the group of the general formula (II), in which $R_1$ is aryl, alkylaryl and alkyl group with $C_1$ to $C_4$ atoms, and n is 0 and 1, and also covers the compounds of the general formula (I), where R is the group of the formula (II), in which $R_1$ is aryl and alkylaryl group, and n is 0 and 1.

According to this invention by condensation of N-substituted derivatives of N-methyl-3-phenyl-3-hydroxypropylamine (XV), where $R_1$ is benzyl and p-nitrobenzyl group and n is 0, and p-trifluoromethylchlorbenzene (XVI) prepared N-substituted derivatives of N-methyl-3-(p-trifluoromethylphenoxy)-3-phenylpropylamine (I), where R is the group of the formula (II), in which n and R are the same as in the compound (XV), which by the reaction with chloroformic acid ester (XVII), where $R_1$ aryl, alkylaryl and alkyl group with $C_1$ to $C_4$ atoms, are converted to N-substituted derivatives of N-methyl-3-(p -trifluoromethylphenoxy)-3-phenylpropylamine (I), where R is the group of the formula (II), in which $R_1$ is the same as in the compound (XVII), and n is 1, from which is prepared the compound of the formula (I), in which R is hydrogen (Fluoxetin), by basic hydrolysis and/or catalytic hydrogenolysis, when R is the group of the formula (II), in which $R_1$ is benzyl and p-nitrobenzyl group, and n is 0 and 1.

18 Claims, No Drawings

N-SUBSTITUTED DERIVATIVES OF N-METHYL-3-(P-TRIFLUOROMETHYLPHENOXY)-3-PHENYLPROPYLAMINE AND THE PROCEDURE FOR THEIR PREPARATION

TECHNICAL FIELD

The invention provides the N-substituted derivatives of N-methyl-3-(p-trifluoromethylphenoxy)-3-phenylpropylamine of the general formula (I),

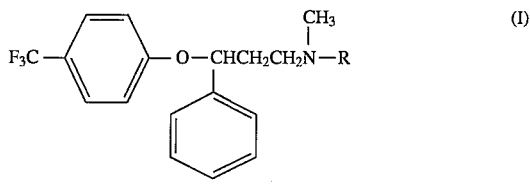

where R is hydrogen and the group having the general formula (II),

$-(CO_2)_nR_1$          (II)

in which $R_1$ is aryl, alkylaryl and alkyl group with $C_1$ to $C_4$ atoms, and n is 0 and 1.

BACKGROUND ART

The compound of the general formula (I,) where R is hydrogen and n is 0 [N-Methyl-3-(p-trifluoromethylphenoxy)-3-phenylpropylamine hydrochloride; Fluoxetin] is used in medicine as a selective inhibitor of serotonine uptake (Wong, D. T., et al., Drug Dev. Res., 1985, 6.397) and in the treatment of depressions and various types of psychical and metabolic disorders (Chovinard, G. A., Clin. J. Psychiatry, 1985.46 32.

Preparation of Fluoxetin is described in the U.S. Pat. Nos. 4,018,895, 4,194,009 and 4,314,081, British Patent 2,060,618, Spanish Patent 556,009 and European Patent Applications (A1) 0 380 924 and 0 391 070.

According to the U.S. patent by bromination of 3-chloropropylbenzene (II) with bromosuccinimide 1-bromine-3-chloropropylbenzene (III) is prepared, which is then by the reaction with p-trifluoromethylphenole converted to N-methyl-(p-trifluoromethylphenoxy)-3-phenylpropylchloride (IV), from which fluoxetin (I) by the reaction with methylamine is obtained.

Yields in the last two phases are moderate, irrespective of the mode in which the process is carried out. Transformation of the compound (IV) into Fluoxetin requires high reaction temperatures at which several by-products are produced, which reduces the yield significantly and creates a considerable problem in obtaining pure product by crystallization.

Significant difficulties also arise during the large scale production which applies another described procedure involving N,N-dimethyl-3-(p-trifluoromethylphenoxy)-3-phenylpropylamine (V) as an intermediate, especially because of the use of bromine cyan as a demethylation agent which is very dangerous under the production conditions. Similarly, yields at some phases of this procedure, according to the statements of EP Appl. 0 391 070 (A1) are very low, approximately 20%.

In the Spanish Patent 556 009, N-acyl and N-alkylcarbalcoxy derivatives of N-methyl-3-phenyl-3-hydroxypropylamine (VI) as intermediates are used, which by the treatment with methylsulfonylchloride are converted into the corresponding methylsulfonyl derivative (VII). After the reaction VII with p-trifluoromethylphenol N-methyl-N-acyl (i.e., alkylcarbalcoxy)-3-(p-trifluoromethylphenoxy)-3-phenylpropylamines (VIII) are obtained, from which Fluoxetin (I) by the acid hydrolysis is prepared.

This procedure too is rather inappropriate for preparation of fluoxetin because it is quite certain that the preparation of starting intermediate (VI), for which there is no indication as of its mode of preparation, requires at least three reaction stages. Furthermore, the compound (VII) is rather unstable, and after all the yields at some phases are in general unsatisfactory. We have experimentally shown that by acid hydrolysis of the compound (VIII), prepared according to the procedure of this invention and under the conditions given in this patent, practically major part of the substance has not been affected by the reaction, and that Fluoxetin has been detected only by thin layer chromatography.

Recently published European Patent Application 0 380 924 (A1) describes preparation of Fluoxetin, where the starting material is ethyl benzoylacetate (IX), from which by the reduction with metal hydrides 3-hydroxy-3-phenylpropionate (X) is obtained. By further reaction with methylamine, it is transformed into N-methylamide 3-hydroxy-3-phenylpropionic acid (XI). This compound (XI) is converted with p-trifluoromethylphenol in the presence of the activating substances to 3-phenyl-3-(p-trifluoromethylphenoxy)-N-methyl propanamide (XII). After the reduction with metal hydrides it gives Fluoxetin (I).

The disadvantage of these procedures is in that, like in already described procedures, one of the starting compounds is the extremely costly p-trifluoromethylphenol (whereas the procedure given in this invention uses much cheaper p-trifluoromethylchlorbenzene), and that it is very unsuitable for the large scale production because of the use of $LiAlH_4$.

In the British Patent 2,060,618 and EP Application 0 391 070 (A1), the starting intermediate is N-methyl-3-phenyl-3-hydroxypropylamine (XIV). Its preparation is described only in the aforementioned EP Appl. and is done by the reduction of b-N-benzyl-N-methylaminopropyophenone (XIII) with hydrogen and Pt-Pd/C as a catalyst. Fluoxetin (I) is produced by the reaction of the compound (XIV) with p-trifluoromethylfluorbenzene in dimethylsulfoxide and NaH (Brit. pat.), i.e., with p-trifluoromethylchlorbenzene in N-methylpyrrolidinone with potassium-terc. butoxide (EP Appl.).

Disadvantage of these procedures is that in the first case one of the starting raw materials is p-trifluoromethylfluorbenzene, which is approximately ten times as expensive as p-trifluoro-methylchlorbenzene. In the second case, the yields at the second phase, according to our experience, are almost by 30% lower than stated in the patent application.

The compounds of the general formula (I), where R is aryl and alkylaril group, and where n is 0 and 1, can be used as intermediates for preparation of Fluoxetin and other pharmacologically active substances.

SUMMARY OF THE INVENTION

Main issue of this invention is the procedure for preparation of the compounds of the general formula (I) in which R have the aforesaid meaning, as well as the compounds of the general formula (I), where R is the group of the formula (II), in which $R_1$ is aryl and alkylaryl group, and n is 0 and 1.

According to the procedure contained in this invention, the compounds of the general formula (I) can be easily prepared and high yields achieved if N-substituted derivatives of N-methyl-3-phenyl-3-hydroxypropylamine of the general formula (XV),

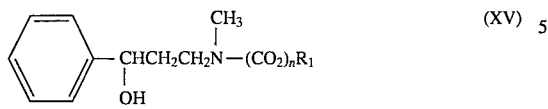

where $R_1$ is benzyl and p-nitrobenzyl group, and n is 0, are etherified with p-trifluoromethylchlorbenzene having formula (XVI),

which give N-substituted derivatives of N-methyl-3-(p-trifluoromethylphenoxy)-3-phenylpropylamine having the general formula (I), where R is the group of the formula (II), in which n and R are the same as in the compound (XV), which are then by the reaction with chloroformic acid ester having the general formula (XVII),

where $R_1$ is aryl, alkylaryl and alkyl group with $C_1$ to $C_4$ atoms (e.g. methyl, ethyl, and butyl group), transformed into the compounds of the general formula (I), where R is the group of the formula (II), in which $R_1$ is the same as in the compound (XVII), and n is 1, and from it the compound of the formula (I), where R is hydrogen, is prepared by basic hydrolysis, and/or catalytic hydrogenolysis, wherein $R_1$ is benzyl and p-nitrobenzyl group, and n is 0 and 1, which is then by the known way of treatment with acids (e.g. hydrochloric and oxalic acids) transformed into corresponding salts.

BEST AND VARIOUS MODES FOR CARRYING OUT INVENTION

The procedure is characterized by the following properties:

a) etherification of the compounds (XV) is carried out at the temperature from 60°–130° C. (optimal temperature 110°–130° C.) for 3–10 hours in the stream of nitrogen, with 0–50% molar excess of p-trifluoromethylchlorbenzene (XVI) in N,N-dimethylacetamide, which are easily regenerated by distillation after the reaction is finished and can be reused in next experiment, giving the highest purity compound of formula (I), where R is the group of the formula (II), in which n and R are the same as in the compound (XV), under the yield of up to 90%;

b) the compounds (I), where R is as the above, are treated with 0–50% molar excess of chloroformic acid ester (XVII) in the aprotic solvents (e.g. toluene, xylene, methylene chloride) at the temperature from 20°–115° C. for 2–5 hours, during which after evaporation and crystallization from a suitable solvent (e.g. lower alcohols, petroleum ether, cyclohexane) produced are N-substituted derivatives of the same general formula (I) and of the highest purity, where R is the group of the formula (II), in which the $R_1$ is the same as in the compound (XVII), and n is 1, to yield up to 92%;

c) the compounds (I) in which R is the group of the formula (II), in which $R_1$ is benzyl and p-nitrobenzyl group, and n is 0 and 1, are subjected to catalytic hydrogenolysis using Pd/C as a catalyst until hydrogen is theoretically used up, in the lower alcohol (e.g. methanol, ethanol) under the normal atmospheric pressure and at room temperature, and/or c1), where R is the group of the formula (II), in which $R_1$ is the same as in the compound (XVII), and n is 1, are subjected to basic hydrolysis with the use of sodium- or potassium-hydroxide, in the diluted lower alcohol with $C_1$ to $C_5$ atoms (e.g. methanol, ethanol, 1-butanol) at 60°–130° C. (optimal temperature 110°–130° C.) during 5–10 hours; during which after the reaction is finished, the solvent is regenerated, treatment with hydrochloric or oxalic acid is done, and crystallization of the crystals performed from ethyl acetate or the mixture of ethyl acetate-ethanol, a pure compound of the formula (I) is obtained, in which R is hydrogen (Fluoxetin), as hydrochloride, i.e. oxylate, under the yields of up to 83%.

The starting compound (XV) can be prepared in quantitative yields, using alkaline solution of $NaBH_4$ as the agent for reduction of β-N-benzyl-N-methylpropiophenone hydrochloride, which is prepared according to somewhat modified procedure of Manich condensation of acetophenone, paraformaldehyde and N-benzyl-M-methylamine hydrochloride in 1-butanol or water.

It has also been shown that the reaction between N,N-dimethyl derivative (V) and chlorformic acid ester (XVII) gives sometimes very stable quaternary ammonium salts, not the corresponding N-methyl-N-alkoxycarbonyl derivatives (M. Matzner, R. P. Kurkjy and R. J. Cotter, Chem. Rew., 64 (1964) 645; B. J. Calvert and J. D. Hobson, J. Chem. Soc., 1965, 2723), from which it comes out that N-benzyl- and N-p-nitrobenzyl derivatives of N-methyl-3-(p-trifluoromethylphenoxy)-3-phenylpropylamihe are much more suitable substrates for the preparation of N-methyl-N-alkoxycarbonyl derivatives (I), than the corresponding N,N-dimethyl derivative (V). The advantage of this procedure, compared to the aforementioned ones, is that it offers a more economical (requires very cheap and easily provided starting raw materials), simple and safe large-scale production of the required intermediates and finished product.

The procedure is illustrated by the below examples which do not limit it at any point.

Example 1

N-benzyl-N-methyl-3-(p-trifluoromethylphenoxy)-3-phenylpropyl-amine

The solution of N-benzyl-N-methyl-3-phenyl-3-hydroxypropylamine (2.55 g, 0 01 mol) in N.N-dimethylacetamide (8 ml) is added dropwise to the suspension of sodium hydride (0.43 g 60% oil dispersion, 0.011 mol) in N.N-dimethylacetamide (6 ml) and heated at 70°–75° C. for 5–10 minutes. To the obtained mixture p-trifluoromethylchlorbenzere (2.1 g, 0.0115 mol) is added and the obtained reaction mixture is heated at 130°–135° C. for 6 hours, then evaporated in vacuo and the residue dissolved in toluene (12 ml). The solution is washed with water (4×5 ml), organic layer filtered and then is added dropwise under mixing 2N hydrochloric acid (12 ml), and cooled at 5°–10° C. for 2–3 hours. The white crystals are filtered and washed firstly with water (10 ml) and then with toluene (10 ml). Obtained product (3.92 g, m.p. 155°–156° C.) is mixed in 1N sodium hydroxide (20 ml) for 10 minutes at 60°–70° C., extracted with toluene (25 ml), then the organic layer is washed with water (4×10 ml), filtered and evaporated in vacuo to give N-benzyl-N-methyl-3-(p-trifluoromethylphenoxy)-3-phenyl-propylamine 3,59 g (90.0%) m.p. 42°–44° C.

IR (KBr): 2970 w, 1620 m, 1520 m, 1460 m, 1330 vs, 1250 s, 1210 vs, 1175 s, 1070 s, 835 m, 700 s, cm$^{-1}$;

$^1$H NMR 300 MHz (CDCl$_3$) d: 1.96–2.05 (2 H, m, CH$_2$), 2.22 (3 H, s, NMe 2.39–2.48 and 2.57–2.64 (2 H, m, CH$_2$), 3.47 and 3.51 (2 H, 2d, J 12 Hz, CH$_2$Ph), 5.32 (1 H, dd, CH), 6.86 (2 H, d, J 8.6 Hz, arom.), 7.22–7.30 (10 H, m, 2 C$_6$H$_5$), 7.41 (2 H, d, J 8.6 Hz, arom.);

Anal.: C$_{24}$H$_{24}$F$_3$NO (399.46)

Calc.: C 72.16; H 6.06; N 3.51%

Found: C 72.18; H 6.34; N 3.54%

Example 2

Methyl N-methyl-3-(p-trifluoromethylphenoxy)-3-phenylpropyl-amine-N-carboxylate The solution of N-benzyl-N-methyl-3-(p-trifluoromethylphenoxy) -3-phenylpropylamine (4.0 g, 0.01 mol) and methyl chloroformate (1.45 g 98%, 0.015 mol) is heated in toluene (50 ml) in a small sealed tube at 110°–115° C. for 4 hours. After the reaction solution is cooled it is firstly washed with 0.1N hydrochloric acid (4×10 ml) and then with 0.1N sodium hydroxide (4×10 ml). Finally organic layer is washed with water (4×10 ml), evaporated in vacuo and residue recrystallized from petroleum ether (12 ml). Yield of methyl N-methyl-3-(p-trifluoromethylphenoxy)-3-phenylpropylamine-N-carboxylate is 3,3 g (90%), m.p. 72°–74° C.

IR (KBr): 2960 w, 1710vs, 1620 s, 1490 m, 1410m, 1375 m, 1340 vs, 1275 vs, 1165 vs, 1070 s, 845 vs, 700 s cm$^{-1}$;

300 MHz $^1$H NMR (CDCl$_3$) d: 2.09–2.10 (2 H, br, CH$_2$), 2.94 (3 H, s, NMe, 3.48 3.65 (5 H, br, CO$_2$Me and CH$_2$), 5.13–5.19 (1 H, br, CH), 6.9 (2 H, d, J 8.6 Hz, arom.), 7.25 –7.35 (5 H, m, C$_6$H$_5$), 7.4 (2 H, d, J 8.6 Hz, arom.);

Anal.: C$_{19}$H$_{20}$F$_3$NO$_3$ (367.36)

Calc.: C 62.11; H 5.49; N 3.81%

Found: C 62.33; H 5.63; N 3.79%

Example 3

Phenyl N-methyl-3-(p-trifluoromethylphenoxy)-3-phenylpropyl-amine-N-carboxylate The solution of N-benzyl-N-methyl-3-(p-trifluoromethylphenoxy) -3-phenylpropylamine (4.0 g, 0.01 mol) and phenyl chloroformate (1.76 g 98%, 0.011 mol) in methylene chloride (50 ml) is mixed at room temperature for 3 hours, and the reaction solution is treated as described in the procedure under Example 2. Yield of pure phenyl N-methyl-3-(p-trifluoromethylphenoxy)-3-phenylpropyl-amine-N-carboxylate is 3,71 g (propanol, 86,5%), m.p. 83°–84° C.

IR (KBr): 2940 w, 1715 vs, 1620 s, 1580 m, 1410 vs, 1340 vs, 1260 vs, 1190 vs, 1050 vs, 947 s, 835 s, 700 s cm$^{-1}$;

300 MHz $^1$H NMR (CDCl$_3$) d: 2.16–2.35 (2 H, m, CH$_2$), 3.02 and 3.09 (3 H, 2s 3.49–3.69 and 3.78–3.85 (2 H, 2m, CH$_2$), 5.23–5.26 (1 H, br, CH), 6.84 (2 10.5 Hz, arom.), 6.90–7.35 (10 H, m, 2 C$_6$H$_5$), 7.42 (2 H, d, J 10.5 Hz, arom.);

Anal.: C$_{24}$H$_{22}$F$_3$NO$_3$ (429.42)

Calc.: C 67.12; H 5.16; N 3.26%

Found: C 67.38; H 5.36; N 3.38%

Example 4 p-Nitrophenyl N-methyl-3-(p-trifluoromethylphenoxy)-3-phenyl-propylaminecarboxylate According to the procedure described under Example 2, from N-benzyl-N-methyl-3-(p-trifluoromethylphenoxy)-3-phenylpropyl-amine (4.0 g, 0.01 mol) and p-nitrophenyl chloroformate (2,37 g 97%, 0,011 mol) in methylene chloride (50 ml) obtained is 4.36 g (92% amyl alcohol) of p-nitrophenyl N-methyl-3-(p-trifluoro-methylphenoxy)-3-phenylpropylamine -N-carboxylate, m.p. 96°–97° C.

IR (KBr): 2970 w, 1720 vs, 1620 m, 1520 s, 1410 m, 1350 s, 1320 s, 1260 s, 121 1110 s, 840 s, 750 m cm$^{-1}$;

300 MHz $^1$H NMR (CDCl$_3$) d: 2.14–2.35 (2 H, br, CH$_2$), 3.05 and 3.11 (3 H 2s, NMe), 3.49–3.60, 3.64–3.74 and 3.82–3.92 (2 H, 3m, CH$_2$), 5.21–5.29 (1 H 6.86 (2 H, d. J 8.7 Hz, arom.), 6.91 and 6.98 (2 H, 2d, J 9 and 9 Hz, arom.), 7 (5 H, m, C$_6$H$_5$), 7.43 (2 H, d, J 8.7 Hz, arom.), 8.12 and 8.19 (2 H, 2d, J 9; arom.);

Anal.: C$_{24}$H$_{21}$F$_3$N$_2$O$_5$ (474.42)

Calc.: C 60.76; H 4.46; N 5.91%

Found: C 61.03; H 4.37; N 6.20%

Example 5

Benzyl N-methyl-3-(p-trifluoromethylphenoxy)-3-phenylpropyl-amine-N-carboxylate The solution of N-p-nitrobenzyl-N-methyl-3-(p-trifluorome -thylphenoxy)-3-phenylpropylamine (4.43 g, 0.01 mol) and benzyl chloroformate (1.98 g 95%, 0.011 mol) in methylene chloride (50 ml) at the boiling point of the solution is heated for 5 hours and then treated as described in the procedure under Example 2. The residue after evaporation of the toluene layer is chromatographed on the silicagel column, under eluation with the mixture of chloroform-benzene (1:1) solvent to give 3.77 g (85%, R$_f$=0.47) benzyl N-methyl-3-(p-trifluoromethylphenoxy)-3-phenyl-propylamine-N-carboxylate as oil.

IR (KBr(L 2965 w, 1710 rs, 1620 s, 1460 m, 1410 m, 1335 vs, 1255 vs, 1165 vs, 1115 vs, 1075 s, 840 s, 700 s cm$^{-1}$;

300 MHz $^1$H NMR (CDCl$_3$) d: 2.06–2.22 (2 H, br, CH$_2$), 2.93 (3 H, s, NMe). 3.44–3.57 (2 H, br, CH$_2$), 4.86–5.19 (3 H, br, CH and CO$_2$CH$_2$Ph), 6.80–7.14 (4 H, m, arom.):

Anal.: C$_{25}$H$_{24}$F$_3$NO$_3$ (443.45)

Calc.: C 67.70; H 5.46; N 3.16%

Found: C 67.45; H 5.68; N 3.05%

Example 6

N,N-dimethyl-N-benzyl-3-(p-trifluoromethylphenoxy)-3-phenyl-propylammonium

The solution of N,N-dimethyl-3-(p-trifluoromethylphenoxy)-3-phenylpropylamine (3.23 g. 0.01 mol) and benzyl chloroformate (1.98 g 98%, 0.011 mol) in toluene (20 ml) is heated at the boiling point of the mixture for 4 hours and then cooled at 0°–5° for 15 hours. The obtained crystals are filtered and re-crystallized from toluene (20 ml) to give 3.46 g (77%) of N,N-dimethyl-N-benzyl-3-(P -trifluoromethylphenoxy)-3-phenylpropylammonium chloride, m.p. 154°–155° C.

IR (KBr) 3020 w, 2980 w, 1620 s, 1525 s, 1340 vs, 1255 vs, 1160 vs, 1025 vs, 835 vs, 735 s, 705 s cm$^{-1}$;

300 MHz $^1$H NMR (CDCl) d: 2.70–2.81 (2 H, m, $CH_2$), 3.56 (6 H, s, $NMe_2$), 3.91–3.97 and 4.18–4.24 (2 H, 2m, $CH_2$), 5.16 and 5.27 (2 H, 2d, J 12.6 and $CH_2Ph$), 5.73 (1 H, dd, CH, 7.13–7.83 (14 H, m. arom.):

Anal.: $C_{25}H_{27}ClF_3NO$ (449.93)

Calc.: C 66.73; H 6.03; N 3.11; C 17.88%

Found: C 67.02; H 6.15; N 3.06; C 18.08%

Example 7

The solution of methyl N-methyl-3-(p-trifluoromethylphenoxy)-3-phenylpropylamine-N-carboxylate (3.67 g, 0.01 mol) and 10N sodium hydroxide (10 ml) in methanol (100 ml 90%) is heated in the sealed tube at 125°–130° C. for 4 hours and evaporated in vacuo. The residue is dissolved in water (20 ml), the solution is extracted with methyl isobutyl ketone (2×30 ml), the collected organic layer is separated and washed with water to pH 6.5–7 and evaporated. The residue is dissolved in ethyl acetate (50 ml), heated to 70°–75° C. and finally oxalic acid (1 g) is added to give 3.1 g (79%) fluoxetin oxalate, m.p. 182°–183° C., which is according to its IR- and $^1$H NMR spectra identical with standard sample.

Example 8

The solution of ethyl N-methyl-3-(p-trifluoromethylphenoxy)-3-phenylpropylamine-N-carboxylate (3.81 g, 0.01 mol) and potassium hydroxide (4.63 g 85%, 0.07 mol) in the mixture of 1-butanol (50 ml) and water (2.5 ml) is heated at the boiling point for 5 hours, cooled, washed with water (10 ml) and then with 2N hydrochloric acid saturated with sodium chloride (2×10 ml) and finally the organic layer is evaporated in vacuo. The residue is dissolved in the mixture of water-toluene (1:2, 15 ml) and cooled at 0°–5° C. for 2–4 hours. Obtained white crystals are filtered and washed firstly with cold water (2×10 ml) and then with toluene (2×10 ml) to give 2.9 g (83.5%) fluoxetin hydrochloride, m.p. 156°–157° C., which is according to its IR- and $^1$H NMR spectra identical with sample.

Example 9

The solution of p-nitrophenyl N-methyl-3-(p-trifluoromethylphenoxy)-3-phenylpropylamine-N-carboxylate (4.89 g, 0.01 mol) and potassium hydroxide (3.31 g 85%, 0.05 mol) in 1-butanol (50 ml 90%) is heated at the boiling point of mixture for 3 hours, and then treated as described in the Example 7 to give 3.26 g (83%) fluoxetin oxalate, which is identical with the sample from Example 7.

Example 10

The suspension of 10% Pd/C in ethanol (20 ml 96%) in the hydrogen atmosphere at normal atmospheric pressure is allowed to stay for 1.5 hours and then the solution of p-nitrobenzyl N-methyl-3-(p-trifluoromethylphenoxy)-3-phenylpropylamine -N-carboxylate (1.96 g, 0.004 mol) in ethanol (20 ml 96%) is added, and mixed in the atmosphere of hydrogen under the same conditions until theoretical quantity of hydrogen is used up. The suspension is filtered, to the filtrate 5N hydrochloric acid (2 ml) is added, evaporated in vacuo and the residue chromotographed on the column of silicagel under eluation firstly with the mixture of chloroform—benzene (1:1), and then with the mixture of chloroform—benzene (1:1), and then with the mixture of chloroform—methanol (9:3, $R_f$ 0.28) solvent to give fluoxetin hydrochloride, m.p. 155°–156° C., which is identical with the sample from Example 8.

Example 11

According to the procedure in the Example 10, N-benzyl-N -methyl-3-(p-trifluoromethylphenoxy)-3-phenylpropylamine hydrochloride (1.74 g, 0.004 mol) is subjected to catalytic hydrogenolysis. After that the suspension is filtered and the filtrate evaporated in vacuo, to the residue 3N sodium hydroxide (6 ml) is added, and the obtained oily suspension is extracted with toluene (4 ml). The organic layer is washed with water (2×2 ml), then under mixing 2N hydrochloric acid, saturated with sodium chloride (4 ml) is added, and finally cooled at 0°–5° C. for 2–4 hours. Obtained white crystals are filtered, washed firstly with cold water saturated with sodium chloride (2×2 ml), and then with toluene (2×2 ml). After crystallization from ethyl acetate (8 ml) fluoxetin hydrochloride, m.p. 155°–156° C. is obtained, which is identical with the sample from Example 8.

We claim:

1. N-methyl-3-(p-trifluoromethylphenoxy)-3-phenylpropylamine having the general formula (I),

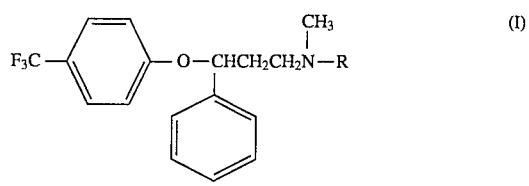

where R has the general formula (II),

in which $R_1$ is selected from the group consisting of aryl, arylalkyl and alkyl group with $C_1$ to $C_4$ atoms, and where n is 0 or 1.

2. The compound according to the claim 1 is characterized by $R_1$ being benzyl, and n being 0.

3. The compound according to the claim 1 is characterized by $R_1$ being p-nitrobenzyl, and n being 0.

4. The compound according to the claim 1 is characterized by $R_1$ being phenyl, and n being 1.

5. The compound according to the claim 1 is characterized by $R_1$ being p-nitrophenyl, and n being 1.

6. The compound according to the claim 1 is characterized by $R_1$ being benzyl, and n being 1.

7. The compound according to the claim 1 is characterized by $R_1$ being p-nitrobenzyl, and n being 1.

8. A method for preparing N-methyl-3-(p -trifluoromethylphenoxy)-3-phenylpropylamine having the general formula (I),

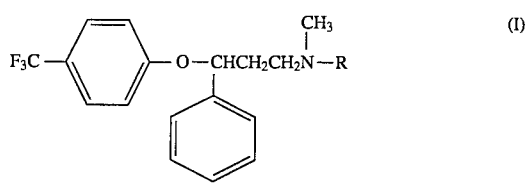

where R is hydrogen or the group of the general formula (II),

in which $R_1$ is selected from the group consisting of aryl, arkylaryl and alkyl group with $C_1$ to $C_4$ atoms and n is 0 or 1, which comprises a) etherifying N-substituted derivatives of N-methyl-3-phenyl-3-hydroxypropylamine of the general formula (XV),

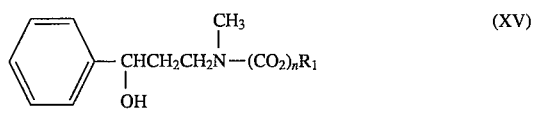

where $R_1$ is benzyl or p-nitrobenzyl group when n is 0, with p-trifluoromethylchlorbenzene having the formula (XVI),

thereby providing N-substituted derivative of N-methyl-3-(p-trifluoromethylphenoxy)-3-phenylpropylamine having the general formula (I), wherein R is the group of the formula (II), in which n and R are the same as in the compound (XV); b) optionally reacting said N-substituted derivatives of N-methyl-3-p-trifluoromethylphenoxy)-3-phenylpropylamine from a) with chloroformic acid ester having the general formula (XVII),

where $R_1$ is selected from the group consisting of aryl, alkylaryl and alkyl group with $C_1$ to $C_4$ atoms, thereby converting the derivative from a) to the compound having the general formula (I), where R is $-(CO_2)_nR_1$, in which $R_1$ is selected from the group consisting of aryl, alkylaryl and alkyl group with $C_1$ to $C_4$ atoms, and n is 1; and optionally preparing the compounds of the formula (I), where R is hydrogen, by basic hydrolysis or catalytic hydrogenolysis or both, when R is $-(CO_2)_nR_1$, in which $R_1$ is benzyl or p-nitrobenzyl group, and n is 0 or 1, and then optionally treating with an acid to form a corresponding salt.

9. The procedure according to the claim 8 is characterized by basic hydrolysis being carded out with sodium- or potassium-hydroxide in a diluted lower alcohol with $C_1$ to $C_5$ atoms (e.g., methyl, ethyl, butyl alcohol) at 60°–120° C.

10. The procedure of claim 9 wherein said lower alcohol is selected from the group consisting of methyl alcohol, ethyl alcohol and butyl alcohol.

11. The procedure according to the claim 8 is characterized by catalytic hydrogenolysis being carried out with Pd/C as a catalyst under normal atmospheric pressure till hydrogen is theoretically used up.

12. The procedure of claim 8 wherein said alkyl group with $C_1$ to $C_4$ atoms is selected from the group consisting of methyl, ethyl and butyl.

13. The method according to claim 8 wherein $R_1$ is benzyl, and n is 0.

14. The method according to claim 8 wherein $R_1$ is p-nitrobenzyl, and n is 0.

15. The method according to claim 8 wherein $R_1$ is phenyl, and n is 1.

16. The method according to claim 8 wherein $R_1$ is p-nitrobenzyl, and n is 1.

17. The method according to claim 8 wherein $R_1$ is benzyl, and n is 1.

18. The method according to claim 8 wherein $R_1$ is p-nitrophenyl, and n is 1.

* * * * *